United States Patent
Lecloux et al.

(10) Patent No.: US 6,963,005 B2
(45) Date of Patent: Nov. 8, 2005

(54) COMPOUNDS COMPRISING PHOSPHORUS-CONTAINING METAL COMPLEXES

(75) Inventors: Daniel David Lecloux, Buellton, CA (US); Nora Sabina Radu, Landenberg, PA (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 37 days.

(21) Appl. No.: 10/631,432

(22) Filed: Jul. 31, 2003

(65) Prior Publication Data

US 2004/0068132 A1 Apr. 8, 2004

Related U.S. Application Data

(60) Provisional application No. 60/403,858, filed on Aug. 15, 2002.

(51) Int. Cl.$^7$ ............... C07F 9/02; B23B 15/00; H01J 1/62
(52) U.S. Cl. ............... 556/22; 313/502; 313/504; 428/690; 428/917
(58) Field of Search ............... 556/22; 428/690, 428/917; 313/502, 504

(56) References Cited

U.S. PATENT DOCUMENTS

| | | |
|---|---|---|
| 2001/0019782 A1 | 9/2001 | Igarashi et al. |
| 2001/0053462 A1 | 12/2001 | Mishima |
| 2002/0022149 A1 | 2/2002 | Watanabe et al. |
| 2002/0024293 A1 | 2/2002 | Igarashi et al. |
| 2002/0034656 A1 | 3/2002 | Thompson et al. |
| 2002/0048689 A1 | 4/2002 | Igarashi et al. |
| 2002/0055014 A1 | 5/2002 | Okada et al. |
| 2002/0063516 A1 | 5/2002 | Tsuboyama et al. |
| 2002/0064681 A1 | 5/2002 | Takiguchi et al. |
| 2002/0068190 A1 | 6/2002 | Tsuboyama et al. |
| 2003/0017361 A1 | 1/2003 | Thompson et al. |
| 2003/0068526 A1 | 4/2003 | Kamatani et al. |

FOREIGN PATENT DOCUMENTS

| | | |
|---|---|---|
| EP | 1 191 612 A2 | 3/2002 |
| EP | 1 191 613 A2 | 3/2002 |
| EP | 1 191 614 A2 | 3/2002 |
| JP | 2003-73387 | 3/2003 |
| WO | WO 00/57676 A1 | 9/2000 |
| WO | WO 00/70655 A2 | 11/2000 |
| WO | WO 01/41512 A1 | 6/2001 |
| WO | WO 02/15645 A1 | 2/2002 |
| WO | WO 02/44188 A1 | 6/2002 |

OTHER PUBLICATIONS

Hiraki et al., Inorganica Chimica Acta, vol. 69, pp. 187–190 (1983).*
Hietkamp, S. et al., Activation of C–H bonds by Transition Metals V. A Study of the Mechanism of Metallation Reactions of Benzyl– and meta–Fluorobenzylphosphines with RhI, IrI, PdII and PtII Compounds, Journal of Organometallic Chemistry, 1979, 351–361, 168, Elsevier Sequoia S.A., Lausanne.
Abicht, Hans–Peter, Darstellung Cyclometallierter, Halogenverbruckter Zweikernkomplexe Des Palladiums und Platins, Journal of Organometallic Chemistry, 1986, 57–61, 311, Elsevier Sequoia S.A., Lausanne.
Newkome, George R. et al., Cyclometalation of the Platinum Metals with Nitrogen and Alkyl, Alkenyl, and Benzyl Carbon Donors, Chem. Rev., 1986, 451–489, 86, American Chemical Society.
Ryabov, Alexander D., Mechanisms of Intramolecular Activation of C–H Bonds in Transition–Metal Complexes, Chem. Rev., 1990, 403–424, 90, American Chemical Society.
Aiello, Iolinda, Synthesis and spectroscopic characterization of organometallic chromophores for photoluminescent materials: cyclopalladated complexes, Journal of Luminescence, 2002, 249–259, 96, Elsevier Science B.V.

* cited by examiner

Primary Examiner—Porfirio Nazario-Gonzalez

(57) ABSTRACT

Compounds comprising phosphorus-containing metal complexes can be used in electroluminescent devices and have an emission maximum closer to the blue region of the visible light spectrum. The complexes can be used within an organic active layer in electronic devices, such as displays, detectors, voltaic cells, solid-state lighting, illumination devices or the like. The complexes may also be used as catalysts or as indicators in other applications. The new compounds can be used without the need of a host material. In non-limiting embodiments, Pt or Ir may be used for the metal atom within the complex, one ligand may include a phosphorus-containing bidentate ligand, and another ligand may include a monoanionic bidentate ligand. The phosphorus-containing bidentate ligand may include a benzyl group, a phenoxy group, a phenylamino group, or the like.

24 Claims, 1 Drawing Sheet

COMPOUNDS COMPRISING PHOSPHORUS-CONTAINING METAL COMPLEXES

This application claims as its priority date Aug. 15, 2003, based on the provisional application Ser. No. 60/403,858, filed Aug. 15, 2002.

BACKGROUND OF THE INVENTION

1. Field of the Invention

The invention relates in general to compounds and electronic devices comprising metallic complexes, and more particularly, to compounds comprising Group 8–10 metallic complexes and their use as active layers within electronic devices, as indicators, and as catalysts.

2. Background

Organic electronic devices that emit light, such as light-emitting diodes as used in displays, are present in many different kinds of electronic equipment. In many of these devices, an organic active layer is sandwiched between two electrical contact layers. At least one of the electrical contact layers is light transmitting so that light can pass through the electrical contact layer. The organic active layer emits light through the light-transmitting electrical contact layer upon application of a voltage across the electrical contact layers.

Organic electroluminescent compounds used as the active component in organic light-emitting diodes ("OLEDs") are well known. Simple organic molecules, such as anthracene, thiadiazole derivatives, and coumarin derivatives are known to be electroluminescent. Semiconductive conjugated polymers have also been used as electroluminescent components. Complexes of 8-hydroxyquinolate with trivalent metal ions, particularly aluminum, have been extensively used as electroluminescent components.

Phosphorescent metal complexes, such as fac-tris(2-phenylpyridine) iridium can be used as the active component in OLEDs. A conventional belief is that in order to achieve efficient devices with phosphorescent metal complex emitters, the emitter must be doped in a charge-transporting host material. In one specific conventional OLED, the active layer can be poly(N-vinyl carbazole) doped with fac-tris[2-(4',5'-difluorophenyl)pyridine-$C'^2$,N]iridium(III). Other electroluminescent devices with an active layer of polymer doped with organometallic complexes of iridium or platinum have been disclosed. However, most of these complexes have emission spectra with peaks in the green or green-blue region. A continuing need exists for electroluminescent compounds having an emission maximum closer to the blue region of the visible light spectrum.

SUMMARY OF THE INVENTION

Compounds comprising phosphorus-containing metal complexes can be used in electroluminescent devices and have an emission maximum closer to the blue region of the visible light spectrum compared to conventional compounds. The complexes can be used within an organic active layer in electronic devices, such as displays, detectors, voltaic cells, solid-state lighting, illumination devices or the like. The complexes may also be used as catalysts or as indicators in other applications. The new compounds can be used without the need of a host material.

In one set of embodiments, a compound can comprise a complex, wherein the complex comprises a metal atom and a phosphorus-containing bidentate ligand. The metal atom can be selected from Os, Ru, Rh, Pd, Ir, and Pt, and the bidentate ligand can comprise a phosphorus atom and a group selected from a benzyl group, a phenoxy group, and a phenylamino group. In each of those groups, a first atom is bonded to the phenyl group, wherein the first atom is selected from carbon, nitrogen, and oxygen. The phosphorus atom may be bonded to the first atom and the metal atom. The metal atom may be bonded to a second atom, wherein the second atom is a carbon atom that is part of the phenyl group.

In another set of embodiments, the compound can comprise a chemical formula selected from Formula 1 and Formula 2:

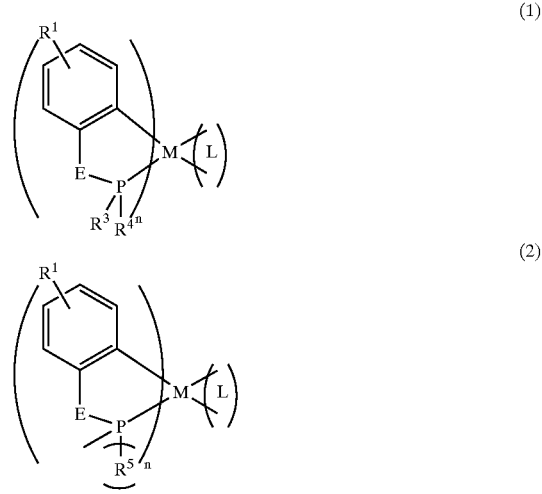

wherein:

M is selected from Os, Ru, Rh, Pd, Ir, and Pt;

L is a monoanionic bidentate ligand;

E is selected from $C(R^2)_2$, O, and $NR^2$;

$R^1$ is selected from hydrogen, deuterium, halogen, alkyl, heteroalkyl, alkoxy, aryl, heteroaryl, and aryloxy;

$R^2$ is selected from alkyl, heteroalkyl, aryl, heteroaryl, and hydrogen;

$R^3$ is selected from aryl, heteroaryl, alkyl, heteroalkyl, alkoxy and aryloxy;

$R^2$ and $R^3$ together may form a 5- or 6-membered ring;

$R^4$ is selected from aryl, heteroaryl, alkyl, heteroalkyl, alkoxy and aryloxy;

$R^5$ is selected from alkyleneoxy, aryleneoxy, biarylene, bialkyl, bialkyloxy, and biaryloxy; and n is selected from 1 and 2.

In a further set of embodiments, the compound can comprise Formula 3 below:

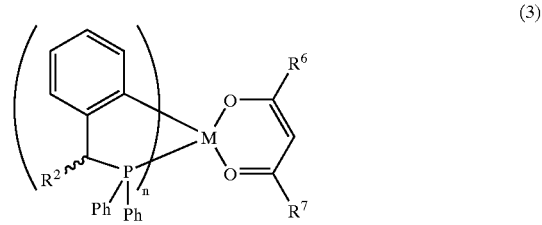

wherein:

M is selected from Ir and Pt;

Ph is a phenyl group;

$R^2$ is selected from methyl and hydrogen;

$R^6$ is an alkyl;

$R^7$ is an alkyl; and n is 1 when M is Pt, and n is 2 when M is Ir.

After reading this specification, skilled artisans appreciate that these specific embodiments are not limiting but illustrate just some of the possible embodiments. The foregoing general description and the following detailed description are exemplary and explanatory only and are not restrictive of the invention, as defined in the appended claims.

BRIEF DESCRIPTION OF THE DRAWINGS

The invention is illustrated by way of example and not limitation in the accompanying figures.

Figure 1:
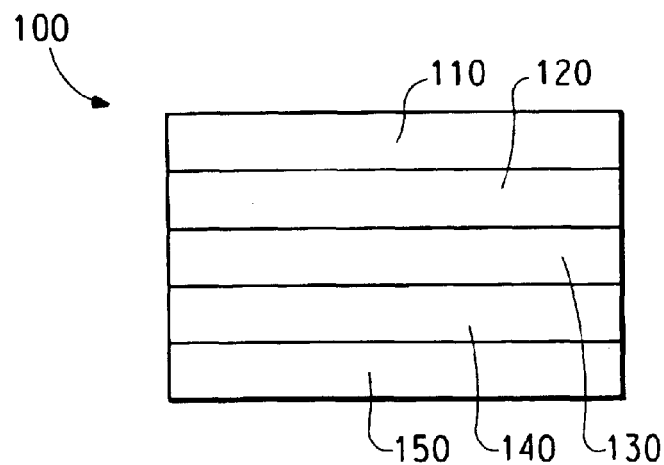
FIG. 1 includes an illustration of a cross-sectional view of an electronic device that includes a benzylphosphine metal complex in an active layer.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

Reference is now made in detail to the exemplary embodiments of the invention, examples of which are illustrated in the accompanying drawings. Wherever possible, the same reference numbers will be used throughout the drawings to refer to the same or like parts (elements).

Compounds comprising phosphorus-containing metal complexes can be used in electroluminescent devices and have an emission maximum closer to the blue region of the visible light spectrum compared to conventional compounds. The complexes can be used within an organic active layer in electronic devices, such as displays, detectors, voltaic cells, solid-state lighting, illumination devices or the like. The complexes may also be used as catalysts or as indicators in other applications. The new compounds can be used without the need of a host material. In non-limiting embodiments, Pt or Ir may be used for the metal atom within the complex, one ligand may include a phosphorus-containing ligand, and another ligand may include a monoanionic bidentate ligand. The phosphorus-containing ligand may include a benzyl group, a phenoxy group, a phenylamino group, or the like. The compound can be used in displays, detectors, voltaic cells, solid-state lighting, illumination devices, and potentially other electronic devices.

Before addressing details of embodiments described below, some terms are defined or clarified. The term "active" refers to any material that exhibits electroluminescence (or other electro-radiative properties) or photosensitivity.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "alkyl" is intended to mean a group derived from an aliphatic hydrocarbon and includes linear, branched and cyclic groups that may be unsubstituted or substituted.

The term "aryl" is intended to mean a group derived from an aromatic hydrocarbon that may be unsubstituted or substituted. The term "alkoxy" is intended to mean a group that includes an oxygen atom bonded to an alkyl sub-group, wherein the oxygen atom forms the bond with the rest of the molecule. The term "aryloxy" is intended to mean a group that includes an oxygen atom bonded to an aryl sub-group, wherein the oxygen atom forms the bond with the rest of the molecule. The term "alkyleneoxy" is intended to mean a bidentate group that includes an oxygen atom bonded to an alkyl sub-group, wherein the oxygen atom forms one bond with the rest of the molecule and the alkyl group forms a second bond with the rest of the molecule. The term "aryleneoxy" is intended to mean a bidentate group that includes an oxygen atom bonded to an aryl sub-group, wherein the oxygen atom forms one bond with the rest of the molecule and the aryl group forms a second bond with the rest of the molecule. Each of the alkoxy, aryloxy, alkyleneoxy, and aryleneoxy groups may be unsubstituted or substituted.

The term "β-dicarbonyl" is intended to mean a neutral compound in which two ketone groups are present, separated by a CHR group. The term "β-enolate" is intended to mean the anionic form of the β-dicarbonyl in which the H from the CHR group between the two carbonyl groups has been abstracted.

The term "benzyl" is intended to mean a group having Fomula (i) and its derivatives.

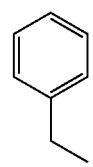

(i)

The term "biarylene" is intended to mean a bidentate group wherein two aryl groups are attached by a single bond with a point of attachment on each aryl group. The term "bialkyl" is intended to mean a bidentate group wherein two alkyl groups are attached by a single bond with a point of attachment on each alkyl group. The term "biaryloxy" is intended to mean a bidentate group wherein two aryloxy groups are attached by a single bond with a point of attachment on the oxygen atom of each aryloxy group. The term "bialkoxy" is intended to mean a bidentate group wherein two alkoxy groups are attached by a single bond with a point of attachment on the oxygen atom of each alkoxy group.

The term "compound" is intended to mean an electrically uncharged substance made up of molecules that further consist of atoms, wherein the atoms cannot be separated from their corresponding molecules by physical means without breaking chemical bonds.

The term "complex", when used as a noun, is intended to mean a compound having at least one metallic atom and at least one ligand. The term "ligand" is intended to mean a molecule, ion, or atom that is attached to the coordination sphere of a metallic atom.

As used herein, the terms "comprises," "comprising," "includes," "including," "has," "having" or any other variation thereof, are intended to cover a non-exclusive inclusion. For example, a method, process, article, or apparatus that comprises a list of elements is not necessarily limited only those elements but may include other elements not expressly listed or inherent to such method, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "electron withdrawing" is synonymous with "hole injecting." Literally, holes represent a lack of electrons and are typically formed by removing electrons, thereby creating an illusion that positive charge carriers, called holes, are being created or injected. The holes migrate by a shift of electrons, so that an area with a lack of electrons is filled with electrons from an adjacent area, which give the appearance that the holes are moving to that adjacent area. For simplicity, the terms holes, hole injecting, and their variants are used herein.

The term "emission maximum" is intended to mean the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively.

The term "group" is intended to mean a part of a compound, such as a substituent in an organic compound or a ligand in a complex.

The term "heteroalkyl" is intended to mean an alkyl group having at least one different atom in place of a carbon atom in the group.

The term "heteroaryl" is intended to mean an aryl group having at least one different atom in place of a carbon atom within the aryl ring. Examples of heteroaryl compounds include furan, pyridazine, thiophene, and the like.

The term "phenylamino" is intended to mean a group having Formula (ii) and its derivatives.

(ii)

The term "phenoxy" is intended to mean a group having Formula (iii) and its derivatives.

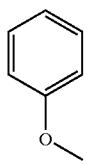

(iii)

The term "photoactive" refers to any material that exhibits electroluminescence or photosensitivity.

The term "polymer" is intended to mean a compound having a molecular weight at least approximately $10^5$ g/mol. The term "small molecule" is intended to mean a compound having a molecular weight no greater than approximately $10^4$ g/mol.

The IUPAC numbering system is used throughout, where the groups from the Periodic Table are numbered from left to right as 1 through 18 (CRC Handbook of Chemistry and Physics, $81^{st}$ Edition, 2000). In the formulae and equations in this specification, the letters E, L, R, and Z may used to designate atoms or groups which are defined within. "Me" is shorthand for a methyl group, "Et" is shorthand for an ethyl group, "Bu" is shorthand for a butyl group, "n-Bu" is shorthand for a normal butyl group, "t-Bu" is shorthand for a tert-butyl group, and "Ph" is shorthand for a phenyl group. Note that Bu can be selected from normal butyl, isobutyl, and tert-butyl groups. All other letters are used to designate conventional atomic symbols. The term "(H+F)" is intended to mean all combinations of hydrogen and fluorine, including completely hydrogenated, partially fluorinated or perfluorinated substituents.

To the extent not described herein, many details regarding specific materials, processing acts, and circuits are conventional and may be found in textbooks and other sources within the organic light-emitting display, photodetector, photovoltaic, and semiconductor arts.

Attention is now directed to more specific details of embodiments that illustrate and not limit the invention. An electronic device can be made with an organic active layer that comprises a compound. The compound can comprise a metallic complex having a chemical formula selected from Formula 1 and Formula 2 below.

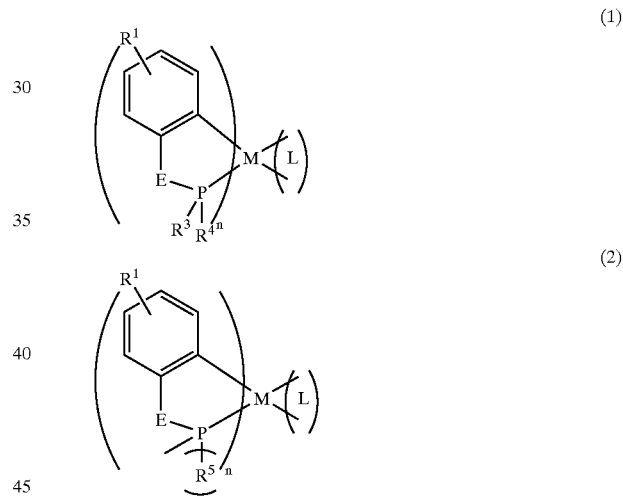

wherein:

M is selected from Os, Ru, Rh, Pd, Ir, and Pt;

L is a monoanionic bidentate ligand;

E is selected from $C(R^2)_2$, O, and $NR^2$;

$R^1$ is selected from hydrogen, deuterium, halogen, alkyl, heteroalkyl, alkoxy, aryl, heteroaryl, and aryloxy;

$R^2$ is selected from alkyl, heteroalkyl, aryl, heteroaryl, and hydrogen;

$R^3$ is selected from aryl, heteroaryl, alkyl, heteroalkyl, alkoxy, and aryloxy;

$R^2$ and $R^3$ together may form a 5- or 6-membered ring;

$R^4$ is selected from aryl, heteroaryl, alkyl, heteroalkyl, alkoxy, and aryloxy;

$R^5$ is selected from alkyleneoxy, aryleneoxy, biarylene, bialkyl, bialkoxy, and biaryloxy; and n is selected from 1 and 2.

The phosphorus-containing ligand shown in Formula (1) and Formula (2) above, may be a benzylphosphine, where $E=C(R^2)_2$, and in Formula (1) $R^3$ and $R^4$ can be the same or different and are independently selected from aryl, heteroaryl, alkyl, and heteroalkyl, and in Formula (2) $R^5$ is selected from biarylene and bialkyl. The benzylphosphines can be obtained from the reaction of the corresponding benzylchloride with a lithium phosphide in a solvent, such as tetrahydrafuran ("THF"). An example of such a reaction is shown as Equation (A) below.

Equation (A)

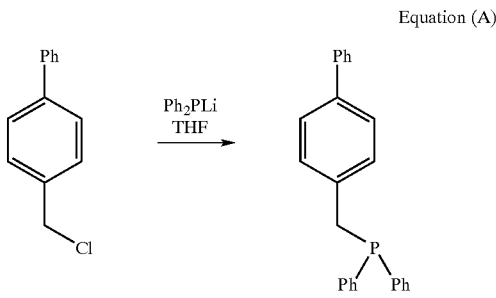

The phosphorus-containing ligand shown in Formula (1) and Formula (2) above, may be a phenylphosphite where E=O, and in Formula (1) $R^3$ and $R^4$ can be the same or different and are independently selected from alkoxy and aryloxy, and in Formula (2) $R^5$ is selected from bialkoxy and biaryloxy. The phenylphosphites can be obtained by the reaction of a chlorophosphite and a phenol in the presence of a base. An example of such a reaction is shown as Equation (B) below:

$(PhO)_2PCl+PhOH+Et_3N \rightarrow PhOP(OPh)_2$     Equation (B)

The phosphorus-containing ligand shown in Formula (1) and Formula (2) above, may be a phenylphosphinite where E=O, and in Formula (1) $R^3$ and $R^4$ can be the same or different and are independently selected from aryl, heteroaryl, alkyl, and heteroalkyl, and in Formula (2) $R^5$ is selected from biaryl and bialkyl. The phenylphosphinites can be obtained by the reaction of a chlorophosphine and a phenol in the presence of a base. An example of such a reaction is shown as Equation (C) below:

$(Ph)_2PCl+PhOH+Et_3N \rightarrow PhOP(Ph)_2$     Equation (C)

The phosphorus-containing ligand shown in Formula (1) and Formula (2) above, may be a phenylphosphonite, where E=O, in Formula (1) $R^3$ is selected from aryl, heteroaryl, alkyl, and heteroalkyl, and $R^4$ is selected from alkoxy and aryloxy, and in Formula (2), $R^5$ is selected from alkyleneoxy and aryleneoxy. The phenylphosphonites can be obtained by the reaction of a dichlorophosphine and a phenol in the presence of a base, followed by the addition of a second phenol and base. An example of such a reaction is shown as Equations (D1) and (D2) below:

$PhPCl_2+PhOH+Et_3N \rightarrow Ph(OPh)PCl$     Equation (D1)

$Ph(OPh)PCl+PhOH+Et_3N \rightarrow PhOP(Ph)(OPh)$     Reaction (D2)

The phosphorus-containing ligand shown in Formula (1) and (2) above, may be a phenylamino phosphorus compound, where $E=NR^2$, and in Formula (1) $R^3$ and $R^4$ can be the same or different and are independently selected from alkoxy, aryloxy aryl, heteroaryl, alkyl, and heteroalkyl, and in Formula (2) $R^5$ is selected from alkyleneoxy, aryleneoxy, biarylene, bialkyl, bialkyloxy, and biaryloxy. The phenylamino phosphorus compounds can be obtained by the reaction of a phenylamino compound with a chlorophosphine or a chlorophosphite. An example of such a reaction is shown as Equation (E) below:

$PhN(Me)H+ClPPh_2+Et_3N \rightarrow PhN(Me)PPh_2$     Equation (E)

An alternative reaction is Equation (F):

$PhN(Me)P(Ph)Cl+ClMgAr \rightarrow PhN(Me)P(Ph)(Ar)$     Equation (F)

The L ligand can be a monoanionic bidentate ligand. In general these ligands have N, O, P, or S as coordinating atoms and form 5- or 6-membered rings when coordinated to a metal atom. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).

The β-enolate ligands generally have Formula 4 below.

(4)

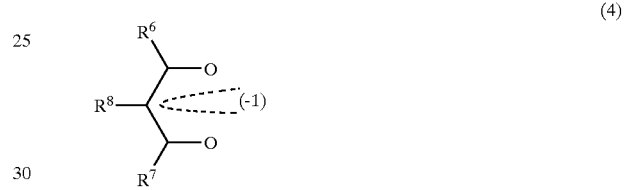

The $R^6$ and $R^7$ groups can be the same or different, and can be hydrogen, halogen, alkyl, heteroalkyl, aryl, or heteroaryl groups. The $R^8$ group can be deuterium, hydrogen, halogen, alkyl, heteroalkyl, aryl, or heteroaryl groups. Adjacent R groups can be joined to form five- and six-membered rings, which can be substituted. For example, $R^6$ and $R^7$ groups may be selected from $—C_m(H+F)_{2m+1}$, $—C_6H_5$, $—C_4H_3S$, and $—C_4H_3O$, where m is an integer from 1 through 12, in a non-limiting embodiment, from 1 to 6. Exemplary $R^8$ groups can include H and F.

Examples of suitable β-enolate ligands include the compounds listed in Table 1 below, where the abbreviation for the β-enolate form is given in brackets.

TABLE 1

| | |
|---|---|
| 2,4-pentanedionate | [acac] |
| 1,3-diphenyl-1,3-propanedionate | [DI] |
| 2,2,6,6-tetramethyl-3,5-heptanedionate | [TMH] |
| 1-(2-thienyl)4,4,4-trifluoroacetonate | [TTFA] |
| 7,7-dimethyl-1,1,1,2,2,3,3-heptafluoro-4,6-octanedionate | [FOD] |
| 1,1,1,5,5,5-hexafluoro-2,4-pentanedionate | [$F_6$acac] |
| 1,1,1,3,5,5,5-heptafluoro-2,4-pentanedionate | [$F_7$acac] |
| 1-phenyl-3-methyl-4-i-butyryl-5-pyrazolinonate | [PMBP]] |

The β-dicarbonyl parent compounds are generally available commercially. The parent compound 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step. This compound can be stored and reacted under anhydrous conditions, as it may be susceptible to hydrolysis.

The hydroxyquinolinate ligands can be substituted with groups, such as alkyl or alkoxy groups which may be partially or fully fluorinated. Examples of suitable hydroxyquinolinate ligands include those in Table 2, with abbreviation provided in brackets:

TABLE 2

| 8-hydroxyquinolinate | [8hq] |
|---|---|
| 2-methyl-8-hydroxyquinolinate | [Me-8hq] |
| 10-hydroxybenzoquinolinate | [10-hbq] |

The parent hydroxyquinoline compounds are generally available commercially.

The phosphino alkoxide ligands generally have Formula 5, shown below,

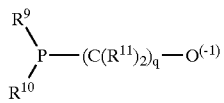

(5)

wherein:
$R^9$ is selected from $C_m(H+F)_{2m+1}$, $C_6(H+F)_pZ_{5-p}$;
$R^{10}$ is selected from $C_m(H+F)_{2m+1}$, $C_6(H+F)_pZ_{5-p}$;
$R^{11}$ can be the same or different at each occurrence and is selected from H, F, and $C_m(H+F)_{2m+1}$;
Z is $C_m(H+F)_{2m+1}$;
m is an integer from 1 through 12;
q is 2 or 3;
p is 0 or an integer from 1 through 5; and The precursor phosphinoalkanol compounds having Formula 6

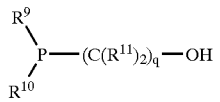

(6)

can be prepared using known procedures, such as, for example, a procedure for preparing 1,1-bis(trifluoromethyl)-2-(diphenylphosphino)ethanol. This method can involve the reaction of diphenylphosphinomethyllithium with hexafluoroacetylacetone, followed by hydrolysis.

Alternatively, the phosphino alkanol compounds can be prepared using the reaction of 1,1-bis(trifluoromethyl) ethylene oxide with the corresponding secondary phosphine ($R^9_2PH$) or its deprotonated form as a salt ($[R^9_2P]M$), where M is Li, Na, or K. The deprotonated form can be prepared by the treatment of the secondary phosphine with a strong base, such as BuLi or t-BuOK.

Alternatively, the phosphino alkanol compounds can be made using dilithiated derivatives of halohydrins, which can be prepared using a conventional method. The dilithio-derivative can be reacted with a chlorophosphine to produce the desired phosphinoalkanol ligand. Halohydrins can be made by a variety of conventional methods, such as ring-opening of an epoxide (also called an "oxirane") with HHal (Hal=Cl, Br, I). This may be useful for preparing 1,1-bis (trifluoromethyl)ethylene oxide. In one embodiment, a dried bromohydrin is combined with n-butyl lithium, wherein the molar ratio of n-butyl lithium to bromohydrin is about 2:1. A process for preparing the phosphino alkanol can comprise:

(1) combining an epoxide with aqueous HBr, to form a bromohydrin;
(2) isolating the bromohydrin from reaction (1) and removing water;
(3) combining the dried bromohydrin from reaction (2) with n-butyl lithium, wherein the molar ratio of n-butyl lithium to the bromohydrin is about 2:1;
(4) adding a chlorophosphine to the product of reaction (3); and
(5) adding acid to the product of reaction (4).

In an exemplary phosphinoalkoxide ligand, $R^9$ and $R^{10}$ are $C_6F_5$ or $C_6H_pY_{5-p}$, where Y is $CF_3$, and p is 3 or 4. In one non-limiting embodiment, at least one of $R^{11}$ is $CF_3$, and q is 2.

Examples of suitable phosphinoalkanol compounds are given in Table 3(a), with the abbreviation in brackets:

TABLE 3(a)

| 1-diphenylphosphino-2-propanol | [dppOH] |
|---|---|
| 1-bis(trifluoromethyl)-2-(diphenylphosphino)ethanol | [PO-1H] |
| 1,1-bis(trifluoromethyl)-2-(bis(3'5'-ditrifluoromethylphenyl)phosphino)ethanol | [PO-2H] |
| 1,1-bis(trifluoromethyl)-2-(bis(4'-trifluoromethylphenyl)phosphino)ethanol | [PO-3H] |
| 1,1-bis(trifluoromethyl)-2-(bis(pentafluorophenyl)phosphino)ethanol | [PO-4H] |

The phosphinoalkoxide ligands corresponding to the above compounds are given in Table 3(b), with the abbreviations provided in brackets:

TABLE 3(b)

| 1-diphenylphosphino-2-propoxide | [dppO] |
|---|---|
| 1-bis(trifluoromethyl)-2-(diphenylphosphino)ethoxide | [PO-1] |
| 1,1-bis(trifluoromethyl)-2-(bis(3'5'-ditrifluoromethylphenyl)phosphino)ethoxide | [PO-2] |
| 1,1-bis(trifluoromethyl)-2-(bis(4'-trifluoromethylphenyl)phosphino)ethoxide | [PO-3] |
| 1,1-bis(trifluoromethyl)-2-(bis(pentafluorophenyl)phosphino)ethoxide | [PO-4] |

A more specific, non-limiting, exemplary set of the metallic complex compounds can comprise Formula 3 below:

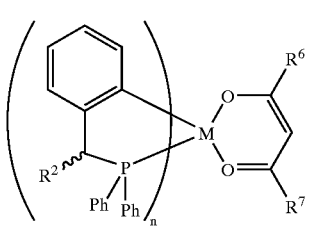

(3)

wherein:
M is selected from Ir and Pt;
Ph is a phenyl group;
$R^2$ is selected from methyl and hydrogen;
$R^6$ is an alkyl;
$R^7$ is an alkyl; and
n is 1 when M is Pt, and n is 2 when M is Ir.

Note than $R^6$ and $R^7$ may be the same or different. In one embodiment, $R^6$ and $R^7$ are independently selected from alkyl groups having from 1 to 4 carbon atoms. Examples of forming some of these compounds are described later in this specification. In any of the formulas described above, a halogen atom, such as fluorine, may be substituted for a hydrogen atom at the same location.

The metal complexes can generally be prepared by combining a metal chloride, a phosphorus-containing ligand, and a monoanionic ligand. The metal chloride can first be reacted with the phosphorus-containing ligand in a suitable solvent, such as 2-ethoxyethanol. For hexacoordinate metals, the ligand to metal molar ratio is generally about 2:1.

For tetracoordinate metals, the ligand to metal molar ratio is generally about 1:1. The resulting intermediate product is then reacted with a salt of the monoanionic ligand, or with the neutral parent compound in the presence of base, to form the complex having Formula 1 or Formula 2.

Attention is now directed to an electronic device comprising the metallic complex and its fabrication process. The electronic device can comprise at least one organic active material positioned between two electrical contact layers, wherein at least one of the layers of the device includes the metallic complex compound. As shown in FIG. 1, the electronic device can comprise an anode layer 110, a cathode layer 150, and an active layer 130. Adjacent to the anode layer 110 is an optional hole-injecting/transport layer 120, and adjacent to the cathode layer 150 is an optional electron-injection/transport layer 140. Layers 120 and 140 are examples of charge transport layers.

The active layer 130 can comprise at least approximately 20 weight percent of a phosphorus-containing metal complex previously described. In some embodiments, the active layer 130 may be substantially 100% of the phosphorus-containing metal complex because a host charge transporting material, such as $Alq_3$ is not needed. By "substantially 100%," it is meant that the metallic complex is the only material in the layer, with the possible exception of impurities or adventitious byproducts from the process to form the layer. Still, in some embodiments, the phosphorus-containing metal complex may be a dopant within a host material, which is typically used to aid charge transport within the active layer 130. The active layer 130, including any of the metallic complexes, can be a small molecule active material.

The device may include a support or substrate (not shown) adjacent to the anode layer 110 or the cathode layer 150. Most frequently, the support is adjacent the anode layer 110. The support can be flexible or rigid, organic or inorganic. Generally, glass or flexible organic films are used as a support. The anode layer 110 is an electrode that is more efficient for injecting holes compared to the cathode layer 150. The anode can include materials containing a metal, mixed metal, alloy, metal oxide or mixed-metal oxide. Suitable metal elements within the anode layer 110 can include the Groups 4, 5, 6, and 8–11 transition metals. If the anode layer 110 is to be light transmitting, mixed-metal oxides of Groups 12, 13 and 14 metals, such as indium-tin-oxide, may be used. Some non-limiting, specific examples of materials for anode layer 110 include indium-tin-oxide ("ITO"), aluminum-tin-oxide, gold, silver, copper, nickel, and selenium.

The anode layer 110 may be formed by a chemical or physical vapor deposition process or spin-cast process. Chemical vapor deposition may be performed as a plasma-enhanced chemical vapor deposition ("PECVD") or metal organic chemical vapor deposition ("MOCVD"). Physical vapor deposition can include all forms of sputtering (e.g., ion beam sputtering), e-beam evaporation, and resistance evaporation. Specific forms of physical vapor deposition include rf magnetron sputtering or inductively-coupled plasma physical vapor deposition ("ICP-PVD"). These deposition techniques are well known within the semiconductor fabrication arts.

A hole-transport layer 120 may be adjacent the anode. Both hole transporting small molecule compounds and polymers can be used. Commonly used hole transporting molecules, in addition to N,N'-diphenyl-N,N'-bis(3-methylphenyl)-[1,1'-biphenyl]-4,4'-diamine (TPD) and bis[4-(N,N-diethylamino)-2-methylphenyl](4-methylphenyl) methane (MPMP), include: 1,1-bis[(di-4-tolylamino) phenyl]cyclohexane (TAPC); N,N'-bis(4-methylphenyl)-N, N'-bis(4-ethylphenyl-[1,1'-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino) benzaldehyde diphenylhydrazone (DEH); triphenylamine (TPA); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N', N'-tetrakis(4-methylphenyl)-(1,1'-biphenyl)-4,4'-diamine (TTB); and porphyrinic compounds, such as copper phthalocyanine. Commonly used hole transporting polymers are polyvinylcarbazole, (phenylmethyl)polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer 120 can be formed using any conventional means, including spin-coating, casting, and printing, such as gravure printing. The layer can also be applied by ink jet printing, thermal patterning, or chemical or physical vapor deposition.

Usually, the anode layer 110 and the hole-injection/transport layer 120 are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer 110 and hole injection/transport layer 120 typically are formed into substantially parallel strips having lengths that extend in substantially the same direction.

The active layer 130 may comprise the metallic complexes described herein. The particular material chosen may depend on the specific application, potentials used during operation, or other factors. The active layer 130 can be applied from solutions by any conventional technique, including spin coating, casting, and printing. The active organic materials can be applied directly by vapor deposition processes, depending upon the nature of the materials.

Optional layer 140 can function both to facilitate electron injection/transport, and also serve as a buffer layer or confinement layer to prevent quenching reactions at layer interfaces. More specifically, layer 140 may promote electron mobility and reduce the likelihood of a quenching reaction if layers 130 and 150 would otherwise be in direct contact. Examples of materials for optional layer 140 include metal-chelated oxinoid compounds (e.g., $Alq_3$ or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like); azole compounds (e.g., 2-(4-biphenylyl)-5-(4-t-butylphenyl)-1,3,4-oxadiazole ("PBD" or the like), 3-(4-biphenylyl)-4-phenyl-5-(4-t-butylphenyl)-1,2,4-triazole ("TAZ" or the like); other similar compounds; or any one or more combinations thereof. Alternatively, optional layer 140 may be inorganic and comprise BaO, LiF, $Li_2O$, or the like.

The electron injection/transport layer 140 can be formed using any conventional means, including spin-coating, casting, and printing, such as gravure printing. The layer can also be applied by ink jet printing, thermal patterning, or chemical or physical vapor deposition.

The cathode layer 150 is an electrode that is particularly efficient for injecting electrons or negative charge carriers. The cathode layer 150 can be any metal or nonmetal having a lower work function than the first electrical contact layer (in this case, the anode layer 110). Materials for the second electrical contact layer can be selected from alkali metals of Group 1 (e.g., Li, Na, K, Rb, Cs,), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer 150 include barium, lithium, cerium, cesium, europium, rubidium, yttrium, magnesium, or samarium.

The cathode layer 150 is usually formed by a chemical or physical vapor deposition process. In general, the cathode layer will be patterned, as discussed above in reference to the anode layer 110 and optional hole injecting layer 120. If the device lies within an array, the cathode layer 150 may be patterned into substantially parallel strips, where the lengths of the cathode layer strips extend in substantially the same direction and substantially perpendicular to the lengths of the anode layer strips. Electronic elements called pixels are formed at the cross points (where an anode layer strip intersects a cathode layer strip when the array is seen from a plan or top view).

In other embodiments, additional layer(s) may be present within organic electronic devices. For example, a layer (not shown) between the hole injecting layer 120 and the active layer 130 may facilitate positive charge transport, band-gap matching of the layers, function as a protective layer, or the like. Similarly, additional layers (not shown) between the electron injecting layer 140 and the cathode layer 150 may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers 120 and 140 are generally of the same type as the active layer 130. More specifically, if the active layer 130 has a small molecule compound, then the charge transport layers 120 and 140, if either or both are present, can have a different small molecule compound. If the active layer 130 has a polymer, the charge transport layers 120 and 140, if either or both are present, can also have a different polymer. Still, the active layer 130 may be a small molecule compound, and any of its adjacent charge transport layers may be polymers.

Each functional layer may be made up of more than one layer. For example, the cathode layer may comprise a layer of a Group 1 metal and a layer of aluminum. The Group 1 metal may lie closer to the active layer 130, and the aluminum may help to protect the Group 1 metal from environmental contaminants, such as water.

Although not meant to limit, the different layers may have the following range of thicknesses: inorganic anode layer 110, usually no greater than approximately 500 nm, for example, approximately 50–200 nm; optional hole-injecting layer 120, usually no greater than approximately 100 nm, for example, approximately 50–200 nm; active layer 130, usually no greater than approximately 100 nm, for example, approximately 10–80 nm; optional electron-injecting layer 140, usually no greater than approximately 100 nm, for example, approximately 10–80 nm; and cathode layer 150, usually no greater than approximately 1000 nm, for example, approximately 30–500 nm. If the anode layer 110 or the cathode layer 150 needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer 140, the electron-hole recombination zone can lie within the $Alq_3$ layer. The emission would then be that of $Alq_3$, and not a desired sharp emission. Thus, the thickness of the electron-transport layer should be chosen so that the electron-hole recombination zone lies within the light-emitting layer (i.e., active layer 130). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer 130 can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material(s) that for their particular applications.

In OLEDs, electrons and holes, injected from the cathode 150 and anode 110 layers, respectively, into the photoactive layer 130, form negative and positively charged polarons in the active layer 130. These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer 110 is biased to a positive voltage and the cathode layer 150 is at substantially ground potential or zero volts during the operation of the electronic device. A battery or other power source(s) may be electrically connected to the electronic device as part of a circuit but is not illustrated in FIG. 1.

In other embodiments, the phosphorus-containing metal complex compound can be used as a charge transport material in layer 120 or 140. The compound does not need to be in a solid matrix diluent (e.g., host charge transport material) when used in layer 120 130, or 140 in order to be effective. A layer greater than approximately 20% by weight of the phosphorus-containing metal complex compound, based on the total weight of the layer, and up to substantially 100% of the complex compound can be used as the active layer 130. Additional materials can be present in the active layer 130 with the complex compound. For example, a fluorescent dye may be present to alter the color of emission. A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

An advantage when using the metallic complexes described above is related to the emission of light closer to blue. When used in a display, the metallic complexes described above can emit light closer to blue. Because of the emission closer to blue, better color control can be from a full-color display. Although some green may be present, users of the display will appreciate blue and violet (using a combination of blue and red subpixels within a pixels) colors closer to their expected colors.

The metallic complexes may be used in applications other than electronic devices. For example, the complexes may be used as catalysts or indicators (e.g., oxygen-sensitive indicators, phosphorescent indicators in bioassays, or the like).

EXAMPLES

The examples include Pt and Ir metallic complexes that can be formed from a number of different chemicals. The last example includes electronic data for some of the compounds described in the examples.

Example 1

The following example is used to exemplify the synthesis of Pt(t-Bu$_2$-acac)(benzyl-diphenylphosphine) from benzyl-diphenylphosphine. The Pt complex can be formed using the pseudo chemical equation, Equation (G) below.

Equation (G)

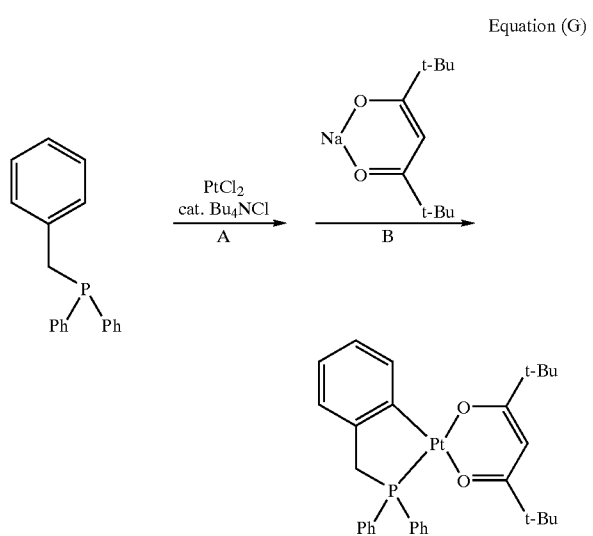

1. "A" reaction. Benzyldiphenylphosphine (approximately 2.0 g or 13 mmol from Strem Chemicals, Inc. of Newburyport, Mass. ("Strem")) and platinum(II) chloride (approximately 1.8 g or 12 mmol; Strem) can be combined in the presence of tetrabutylammonium chloride (approximately 330 mg or 0.12 mmol from Sigma-Aldrich Corp. of St. Louis, Mo. ("Aldrich")) in chlorobenzene (approximately 100 mL; Aldrich) and can be stirred at approximately 130° C. for approximately 10 minutes under nitrogen, after which time the volatile components can be removed in vacuo. The solid residue may be suspended in methanol, and the resulting solid can be isolated via filtration, washed with ether, and allowed to dry in vacuo. The yield of this resulting solid can be approximately 3.5 g.

2. "B" reaction. The entire yield of the resulting solid from the A reaction can be combined with 2,2,6,6-tetramethyl-3,5-heptanedione, sodium salt (approximately 1.8 g or 8.7 mmol that can be prepared from the corresponding acid and sodium hydride (both from Aldrich)) and 2-ethoxyethanol (approximately 50 mL; Aldrich). The contents may be stirred under nitrogen at approximately 120° C. for approximately 45 minutes. The volatile components can then be removed in vacuo. The desired product can be purified from a resulting crude dark brown solid via silica gel flash chromatography with hexanes/ethyl acetate (at a ratio of approximately 20:1) as the eluting solvent (product $R_f$=0.7). The desired product (approximately 250 mg or 0.38 mmol, 3.2% from PtCl$_2$) can be isolated as a colorless foamy solid that exhibits blue luminescence under 254 and 365 nm illumination.

$^1$H NMR (300 MHz, CD$_2$Cl$_2$, 296 K): δ 7.76–7.83 (4H, m), 7.38–7.46 (4H, m), 7.13–7.25 (2H, m), 6.90–7.13 (3H, m), 5.86 (1H, s), 3.71 (2H, d, J=11.6 Hz), 1.29 (9H, s), 1.09 (9H, s) ppm.

Example 2

The following example is used to exemplify the synthesis of Pt(t-Bu$_2$-acac)(4-phenyl-benzyl-diphenylphosphine) from 4-phenylbenzylchloride. The Pt complex can be formed using the pseudo chemical equation, Equation (H), below.

Equation (H)

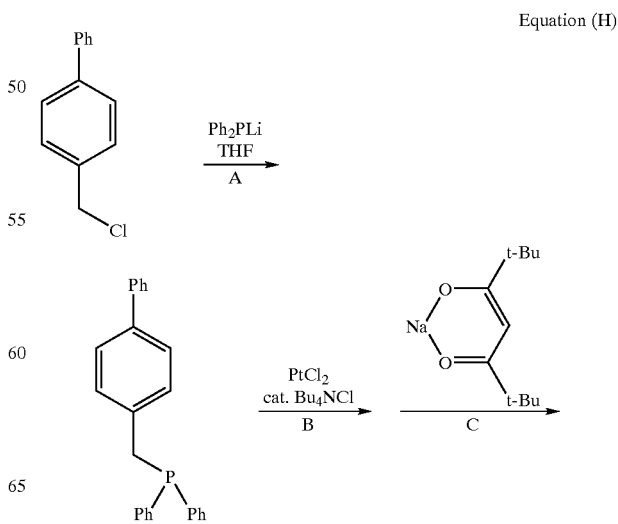

-continued

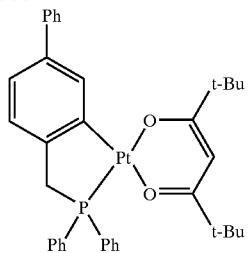

1. "A" reaction. To a stirred solution of 4-phenylbenzylchloride (approximately 1.6 g or 8.1 mmol; Aldrich) in anhydrous THF (approximately 10 mL; Aldrich) under nitrogen at room temperature can be added lithium diphenylphosphide (approximately 1.6 g or 8.1 mmol; prepared from n-butyllithium (Aldrich) and diphenylphosphine (Strem)) in anhydrous THF (approximately 10 mL) dropwise over one minute. The reddish solution of the phosphorous reagent can be bleached upon contact with a benzyl chloride solution. The mixture can then be evaporated to dryness after approximately one hour of stirring. The residue may be extracted with anhydrous/degassed dichloromethane and filtered through celite to remove the precipitated salt byproduct. The filtrate can be evaporated to dryness, to afford the desired product as a crude off-white solid, which can be used for further processing without additional purification. The isolated yield can be approximately 2.5 g (88%).

$^1$H NMR (300 MHz, $CD_2Cl_2$, 296 K): δ 7.35–7.50 (6H, m), 7.30–7.35 (2H, m), 7.15–7.25 (2H, m), 7.05–7.20 (9H, m), 3.29 (2H, s) ppm. 31P NMR (203 MHz, $CD_2Cl_2$, 296 K) δ −8.93 ppm.

2. "B" reaction. The product from the A reaction (approximately 2.0 g or 5.7 mmol), platinum(II) chloride (approximately 1.4 g or 5.2 mmol; Strem), and tetrabutylammonium chloride (approximately 140 mg or 0.52 mmol; Aldrich, dried in vacuo) can be stirred under nitrogen in chlorobenzene (approximately 50 mL, Aldrich) at approximately 130° C. for approximately 10 minutes, after which time the volatile components can be removed in vacuo. The solid residue can be suspended in methanol, and the resulting solid can be isolated via filtration, washed with ether, and allowed to dry in vacuo.

3. "C" reaction. Approximately 1.0 g of the crude solid from the B reaction can be combined with 2,2,6,6-tetramethyl-3,5-heptanedione, sodium salt (approximately 44 mg or 2.2 mmol; prepared from the corresponding acid and sodium hydride (both from Aldrich)) and 2-ethoxyethanol (approximately 50 mL; Aldrich). The contents can be stirred under nitrogen at approximately 120° C. for approximately 45 minutes. The volatile components can be then removed in vacuo, and the desired product may be purified from the resulting crude dark brown solid via silica gel flash chromatography with hexanes/ethyl acetate (at a ratio of approximately 8:1) as the eluting solvent (product $R_f$=0.7). The desired product (approximately 75 mg or 0.10 mmol) can be isolated as a colorless foamy solid that exhibits blue luminescence under 254 and 365 nm illumination.

$^1$H NMR (300 MHz, $CD_2Cl_2$, 296 K): δ 8.18 (1H, m), 7.78–7.90 (4H, m), 7.62–7.68 (2H, m), 7.35–7.50 (9H, m), 7.22–7.33 (3H, m), 5.88 (1H, s), 3.75 (2H, d, J=11.7 Hz), 1.31 (9H, s), 1.10 (9H, s) ppm.

Example 3

The following example is used to exemplify the synthesis of Pt(t-Bu$_2$-acac)((±)1-phenylethyl-diphenylphosphine) from (±)-1-phenylethylchloride. The Pt complex can be formed using the pseudo chemical equation, Equation (I), below.

Equation (I)

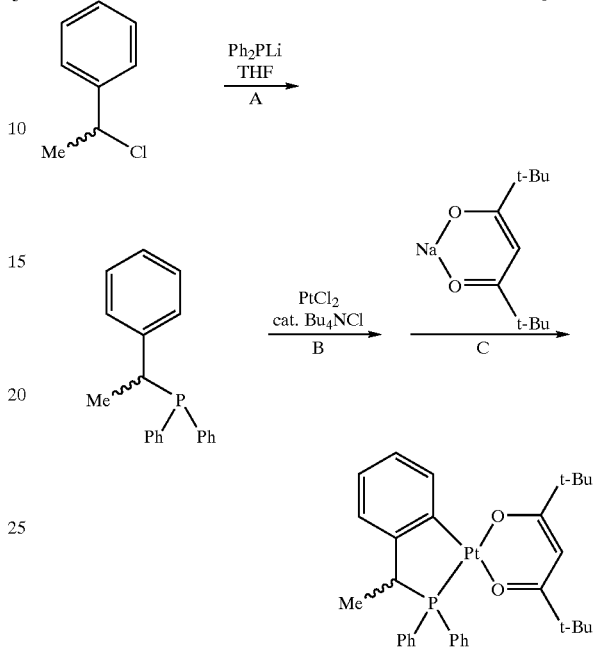

1. "A" reaction. To a stirred solution of (±)-1-phenylethylchloride (approximately 1.5 g or 7.8 mmol available from Acros Organics of Fisher Scientific International, Inc. of Hampton, N.H. ("Acros Organics")) in anhydrous THF (approximately 10 mL; Aldrich) under nitrogen at room temperature can be added lithium diphenylphosphide (approximately 1.5 g or 8.1 mmol; prepared from n-butyllithium (Aldrich) and diphenylphosphine (Strem Chemicals)) in anhydrous THF (approximately 10 mL) dropwise over one minute. The reddish solution of the phosphorous reagent may be bleached upon contact with a benzyl chloride solution. The mixture can be evaporated to dryness after approximately one hour of stirring. The residue may be extracted with anhydrous/degassed dichloromethane and filtered through celite to remove the precipitated salt byproduct. The filtrate can be evaporated to dryness, to afford the intermediate product as a crude off-white solid, which can be used for further chemistry without additional purification. The isolated yield can be approximately 2.0 g (88%).

2. "B" reaction. The product from the A reaction (approximately 1.0 g or 3.5 mmol), platinum(II) chloride (approximately 920 mg or 3.5 mmol; Strem), and tetrabutylammonium chloride (approximately 96 mg or 0.35 mmol; Aldrich, dried in vacuo) can be stirred under nitrogen in chlorobenzene (approximately 50 mL, Aldrich) at approximately 130° C. for approximately 10 minutes, after which time the volatile components can be removed in vacuo. The solid residue may be suspended in methanol, and the resulting solid can be isolated via filtration, washed with ether, and allowed to dry in vacuo.

3. "C" reaction. Approximately 850 mg of the crude solid from the B reaction can be combined with 2,2,6,6-tetramethyl-3,5-heptanedione, sodium salt (approximately 420 mg or 2.0 mmol; prepared from the corresponding acid and sodium hydride (both from Aldrich)) and 2-ethoxyethanol (approximately 50 mL; Aldrich), and the contents can be stirred under nitrogen at approximately 120°

C. for approximately 45 minutes. The volatile components can then be removed in vacuo, and the desired product may be purified from the resulting crude dark brown solid via silica gel flash chromatography with hexanes/ethyl acetate (at a ratio of approximately 8:1) as the eluting solvent (product $R_f$=0.7). The desired product (approximately 210 mg or 0.31 mmol) may be isolated by recrystallization from hexanes, to afford a colorless microcrystalline solid that exhibits blue luminescence under 254 and 365 nm illumination.

$^1$H NMR (300 MHz, CD$_2$Cl$_2$, 296 K): δ 7.79–7.86 (3H, m), 7.58–7.69 (2H, m), 7.33–7.55 (6H, m), 7.10–7.22 (1H, m), 6.90–7.05 (2H, m), 5.86 (1H, s), 3.87 (1H, q, J=3.4 Hz), 1.28 (9H, s), 1.19 (3H, dd, J=17.0 and 7.2 Hz), 1.09 (9H, s).

Example 4

The following example is used to exemplify the synthesis of Pt(t-Bu$_2$-acac)(2-phenyl-benzyl-diphenylphosphine) from 2-phenylbenzylbromide. The Pt complex can be formed using the pseudo chemical equation, Equation (J), below.

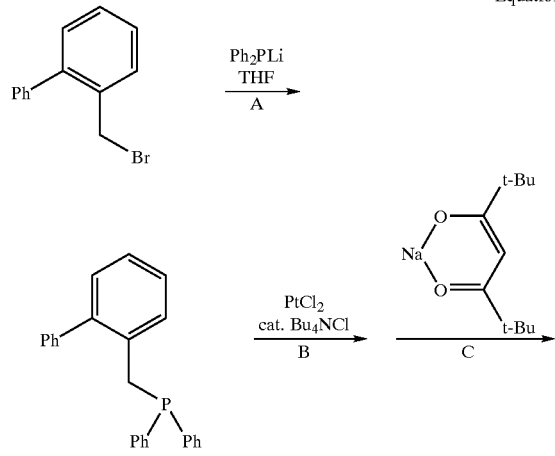

Equation (J)

1. "A" reaction. To a stirred solution of 2-phenylbenzylbromide (approximately 1.9 g or 7.8 mmol; Aldrich) in anhydrous THF (approximately 10 mL; Aldrich) under nitrogen at room temperature can be added lithium diphenylphosphide (approximately 1.5 g pr 7.8 mmol; prepared from n-butyllithium (Aldrich) and diphenylphosphine (Strem Chemicals)) in anhydrous THF (approximately 10 mL) dropwise over one minute. The reddish solution of the phosphorous reagent may be bleached upon contact with a benzyl bromide solution. The mixture can be evaporated to dryness after approximately one hour of stirring. The residue may be extracted with anhydrous/degassed dichloromethane, filtered through celite to remove the precipitated salt byproduct. The filtrate can be evaporated to dryness, to afford the intermediate product as a crude off-white solid, which can be used for further chemistry without additional purification. The isolated yield may be approximately 2.0 g (73%).

$^1$H NMR (300 MHz, CD$_2$Cl$_2$, 296 K): δ 7.05–7.18 (5H, m), 6.85–7.05 (5H, m), 6.70–6.85 (9H, m), 3.23 (2H, s) ppm. 31 P NMR (203 MHz, CD$_2$Cl$_2$, 296 K) δ −7.50 ppm.

2. "B" reaction. A portion of the product from the A reaction (approximately 1.5 g or 4.3 mmol), platinum(II) chloride (approximately 1.1 g or 4.3 mmol; Strem), and tetrabutylammonium chloride (approximately 120 mg or 0.43 mmol; Aldrich, dried in vacuo) can be stirred under nitrogen in chlorobenzene (approximately 50 mL, Aldrich) at approximately 130° C. for approximately 10 minutes, after which time the volatile components can be removed in vacuo. The solid residue can be suspended in methanol, and the resulting solid may be isolated via filtration, washed with ether, and allowed to dry in vacuo.

3. "C" reaction. Approximately 1.9 g portion of the crude solid from the B reaction can be combined with 2,2,6,6-tetramethyl-3,5-heptanedione, sodium salt (approximately 690 mg or 3.4 mmol; prepared from the corresponding acid and sodium hydride (both from Aldrich)) and 2-ethoxyethanol (approximately 50 mL; Aldrich). The contents may be stirred under nitrogen at approximately 120° C. for approximately 45 minutes. The volatile components can then be removed in vacuo. The desired product may be purified from the resulting crude dark brown solid via silica gel flash chromatography with hexanes/ethyl acetate (at a ratio of approximately 8:1) as the eluting solvent (product $R_f$=0.7), and then it can be recrystallized from hexanes. The desired product (approximately 130 mg or 0.17 mmol) may be isolated as a microcrystalline solid that exhibits blue luminescence under 254 and 365 nm illumination.

$^1$H NMR (300 MHz, CD$_2$Cl$_2$, 296 K): δ 7.80–7.88 (1H, d), 7.62–7.75 (3H, m), 7.28–7.52 (10H, m), 7.02–7.13 (2H, m), 6.85–6.95 (2H, m) 5.88 (1H, s), 3.61 (2H, d, J=11.6 Hz), 1.31 (9H, s), 1.10 (9H, s) ppm.

Example 5

The following example is used to exemplify the synthesis of an Ir complex. The Ir complex can be Ir(acac)bis(benzyl-diphenylphosphine), which can be made from benzyldiphenylphosphine. The Ir complex can be formed using the pseudo chemical equation, Equation (K), below.

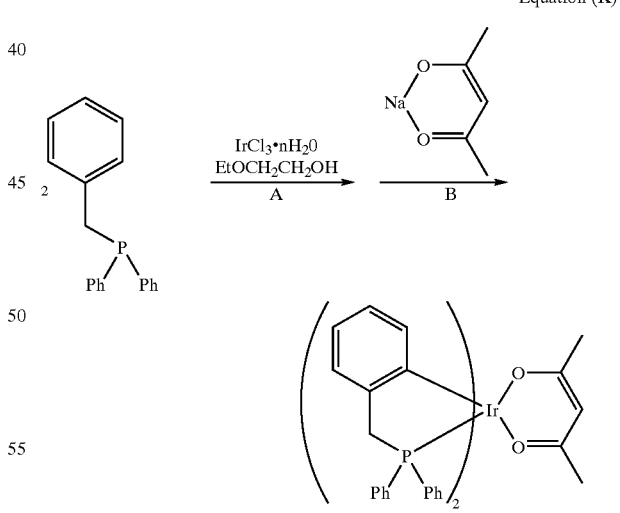

Equation (K)

1. "A" reaction. Benzyldiphenylphosphine (approximately 1.0 g or 3.6 mmol; Strem Chemicals), IrCl$_3$.nH$_2$O (approximately 0.52 g or 1.7 mmol; available from Johnson Matthey Inc. of West Deptford, N.J.), and ethoxyethanol (approximately 15 ml; Aldrich, degassed) can be stirred at approximately 130° C. for approximately 45 minutes under nitrogen. The yellow precipitate may be isolated by filtration and dried under vacuum to yield approximately 0.78 g of the intermediate product.

$^{31}$P NMR (202 MHz, CD$_2$Cl$_2$, 296 K): δ −38.83.

2. "B" reaction. The product from the A reaction (approximately 0.30 g) can be combined with the sodium salt of 2,4-pentanedione (approximately 0.59 g or 0.48 mmol; prepared from the corresponding acid and sodium hydride (both from Aldrich)) and 2-ethoxyethanol (approximately 15 mL; Aldrich), and the contents can be stirred under nitrogen at approximately 130° C. for approximately one hour. The volatile components can then be removed in vacuo, and the product may be purified from the resulting crude off-white solid via silica gel flash chromatography with CH$_2$Cl$_2$ as the eluting solvent. The product (approximately 35 mg) may be isolated as a white solid that exhibits blue luminescence under 254 and 365 nm illumination.

$^{31}$P NMR (202 MHz, CD$_2$Cl$_2$, 296 K): δ −5.28.

Example 6

This example illustrates the formation of OLEDs using the metallic complexes of Examples 1–4 as described above. Thin film OLED devices including a hole transport layer (HT layer), electroluminescent layer (EL layer) and at least one electron transport layer (ET layer) can be fabricated by a thermal evaporation technique. An Edward Auto 306 evaporator (available from BOC Coating Technology division of BOC Edwards of Fairfield, Calif.) with oil diffusion pump may be used. The base vacuum for all of the thin film depositions may be on the order of approximately 10$^{-6}$ torr. The deposition chamber is capable of depositing five different films without the need to break up the vacuum.

An indium tin oxide (ITO) coated glass substrate can be used. The ITO layer may have a thickness in a range of approximately 100–200 nm. The substrate may be first patterned by etching away the unwanted ITO area with a nominal 1M HCl solution to form a first electrode pattern. Polyimide tape can be used as the mask. The patterned ITO substrates may then be cleaned ultrasonically in an aqueous detergent solution. The substrates may then be rinsed with distilled water, followed by isopropanol, and then degreased in toluene vapor for approximately three hours.

The cleaned, patterned ITO substrate can then be loaded into the vacuum chamber that is pumped down to approximately 10$^{-6}$ torr of absolute pressure. The substrate may then be further cleaned using an oxygen plasma for about approximately 5–10 minutes. After cleaning, multiple layers of thin films may then be deposited sequentially onto the substrate by thermal evaporation. Finally, patterned metal electrodes of Al may be deposited through a shadow mask. The thickness of the film may be measured during deposition by using a quartz crystal monitor (Sycon STC-200 available from Sycon Instruments, Inc. of Syracuse, N.Y.). The completed OLED device can be then removed from the vacuum chamber and characterized immediately without encapsulation.

A summary of the device layers and thicknesses is given in Table 4. In all cases the anode is ITO as discussed above, and the cathode is Al having a thickness in the range of approximately 70–76 nm. All thicknesses in Table 1 are approximate.

Figure 2:
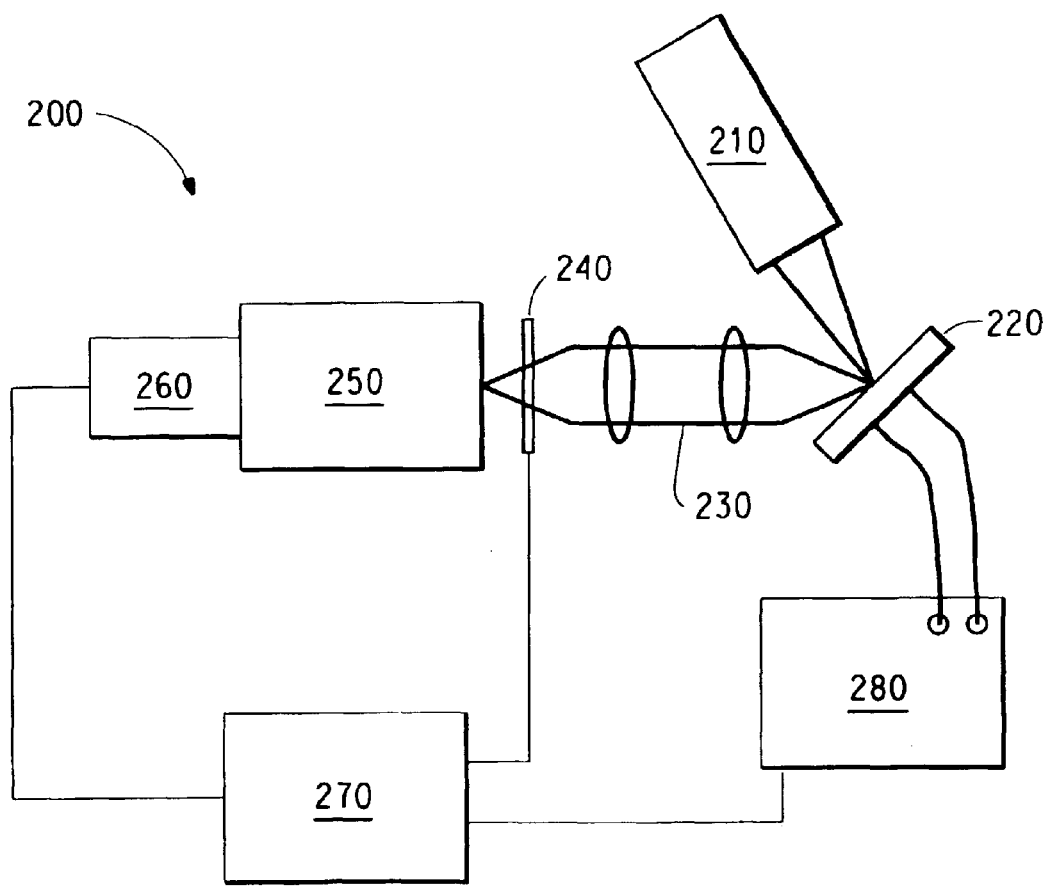
FIG. 2 includes a schematic diagram of an LED testing apparatus.

The OLED samples can be characterized by measuring their (1) current-voltage (I-V) curves, (2) electroluminescence radiance versus voltage, and (3) electroluminescence spectra versus voltage. The apparatus 200 used is shown in FIG. 2. The I-V curves of an OLED sample 220 may be measured with a source-measurement unit 280, such as the Keithley Source-Measurement Unit Model 237 made by Keithley Instruments, Inc. of Solon, Ohio. The electroluminescence radiance (in the unit of Cd/m$^2$) vs. voltage may be measured with luminescence meter 210, such as a Minolta LS-110 luminescence meter available from Minolta Corporation USA of Ramsey, N.J., while the voltage was scanned using the source-measurement unit 280. The electroluminescence spectrum may be obtained by collecting light using a pair of lenses 230 through an electronic shutter 240 dispersed through a spectrograph 250 and then measured with a diode array detector, 260. All three measurements may be performed at the same time and controlled by a computer 270. The efficiency of the device at certain voltage can be determined by dividing the electroluminescence radiance of the LED by the current density needed to run the device. The unit for efficiency is in Cd/A.

The results are given in Table 4 below:

TABLE 4

MPMP = bis[4-(N,N-diethylamino)-2-methylphenyl](4-methylphenyl)methane
DPA = 4,7-diphenyl-1,10-phenanthroline

| Light Emitter | hole transporter | electron transporter | device configuration | LED intensity |
|---|---|---|---|---|
| Example 1 | MPMP | DPA | MPMP (510 Å)/ Example 1 (410 Å)/ DPA (440 Å)/ Al (720 Å) | Peak radiance-30 cd/m$^2$ at 24 V (450 + 590 nm); Peak efficiency- 0.9 Cd/A |

TABLE 4-continued

MPMP = bis[4-(N,N-diethylamino)-2-methylphenyl](4-methylphenyl)methane
DPA = 4,7-diphenyl-1,10-phenanthroline

| Light Emitter | hole trans- porter | electron trans- porter | device configuration | LED intensity |
|---|---|---|---|---|
| Example 2 | MPMP | DPA | MPMP (510 Å)/ Example 2 (270 Å)/ DPA (420 Å)/ Al (720 Å) | Peak radiance- 100 cd/m2 at 24 V (450 + 480 + 590 nm); Peak efficiency- 0.7 Cd/A |
| Example 3 | MPMP | DPA | MPMP (510 Å)/ Example 3 (410 Å)/ DPA (420 Å)/ Al (720 Å) | Peak radiance- 120 Cd/m2 at 21 V (450 + 590 nm); Peak efficiency- 1.5 Cd/A |
| Example 4 | MPMP | DPA | MPMP (520 Å)/ Example 4 (420 Å)/ DPA (410 Å)/ Al (730 Å) | Peak radiance-60 cd/m2 at 22 V (440 + 458 + 590 nm); Peak efficiency- 0.9 Cd/A |

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims.

What is claimed is:

1. An electronic device comprising an active layer A comprising a complex, wherein the complex comprises:
   a metal atom selected from Os, Ru, Rh, Pd, Ir, and Pt; and
   a phosphorus-containing bidentate ligand comprising a phosphorus atom and a group selected from a benzyl group, a phenoxy group, and a phenylamino group, wherein:
   the phosphorus-containing bidentate ligand comprises a phenyl group and a first atom bonded to the phenyl group, wherein the first atom is selected from carbon, nitrogen, and oxygen;
   the phosphorus atom is bonded to the first atom and the metal atom; and
   the metal atom is bonded to a second atom, wherein the second atom is a carbon atom that is part of the phenyl group.

2. The electronic device of claim 1, wherein in the complex the metal atom is selected from Ir and Pt.

3. The electronic device of claim 1 wherein the complex further comprises a monoanionic bidentate ligand bonded to the metal atom.

4. The electronic device of claim 3, wherein the monoanionic bidentate ligand of the complex is selected from β-enolates, aminocarboxylates, iminocarboxylates, salicylates, hydroxyquinolinates and diarylphosphinoalkoxides.

5. The electronic device of claim 1, wherein the complex molecule further comprises a β-enolate ligand bonded to the metal atom.

6. The electronic device of claim 5, wherein the complex comprises:
the first atom bonded to the phenyl group is a carbon atom; and
the β-enolate ligand is selected from:
2,4-pentanedionate;
1,3-diphenyl-1,3-propanedionate;
2,2,6,6-tetramethyl-3,5-heptanedionate;
4,4,4-trifluoro-1-(2-thienyl)-1,3-butanedionate;
7,7-dimethyl-1,1,1,2,2,3,3-heptafluoro-4,6-octanedionate;
1,1,1,3,5,5,5-heptafluoro-2,4-pentanedionate;
1,1,1,5,5,5-hexaflouro-2,4-pentanedionate; and
1-phenyl-3-methyl-4-i-butyryl-pyrazolinonate.

7. The electronic device of claim 1, wherein:
the electronic device comprises a display; and
the complex is capable of having an emission maximum in a range of approximately 420–480 nm.

8. The electronic device of claim 7, wherein the compound comprises at least approximately 20 weight percent of the active layer.

9. An electronic device comprising an active layer comprising a compound comprising a chemical formula selected from Formula 1 and Formula 2:

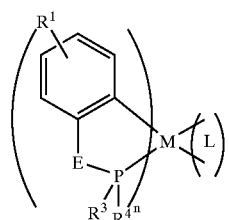

(1)

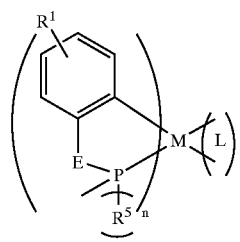

(2)

wherein:
M is selected from Os, Ru, Rh, Pd, Ir, and Pt;
E is selected from $C(R^2)_2$, O, and $NR^2$;
L comprises a monoanionic bidentate ligand;
$R^1$, if present, is selected from hydrogen, deuterium, halogen, alkyl, heteroalkyl, alkoxy, aryl, heteroaryl, and aryloxy;
$R^2$ is selected from alkyl, heteroalkyl, aryl, heteroaryl, and hydrogen;
$R^3$ is selected from aryl, heteroaryl, alkyl, heteroalkyl, alkoxy, and aryloxy;
$R^2$ and $R^3$ together may form a 5- or 6-membered ring;
$R^4$ is selected from aryl, heteroaryl, alkyl, heteroalkyl, alkoxy, and aryloxy;
$R^5$ is selected from alkyleneoxy, aryleneoxy, biarylene, bialkyl, bialkyloxy, and biaryloxy; and
n is selected from 1 and 2.

10. The electronic device of claim 9, wherein M is selected from Ir and Pt.

11. The electronic device of claim 9, wherein each of $R^3$ and $R^4$ is a phenyl group.

12. The electronic device of claim 9, wherein L is selected from β-enolates, aminocarboxylates, iminocarboxylates, salicylates, hydroxyquinolinates and diarylphosphinoalkoxides.

13. The electronic device of claim 12, wherein:
E is a carbon atom; and
L comprises a β-enolate ligand selected from:
2,4-pentanedionate;
1,3-diphenyl-1,3-propanedionate;
2,2,6,6-tetramethyl-3,5-heptanedionate;
4,4,4-trifluoro-1-(2-thienyl)-1,3-butanedionate;
7,7-dimethyl-1,1,1,2,2,3,3-heptafluoro-4,6-octanedionate;
1,1,1,3,5,5,5-heptafluoro-2,4-pentanedionate;
1,1,1,5,5,5-hexaflouro-2,4-pentanedionate; and
1-phenyl-3-methyl-4-i-butyryl-pyrazolinonate.

14. The electronic device of claim 9, wherein:
the electronic device comprises a display; and
the compound is capable of having an emission maximum in a range of approximately 420–480 nm.

15. The electronic device of claim 14, wherein the compound comprises at least approximately 20 weight percent of the active layer.

16. A compound comprising:

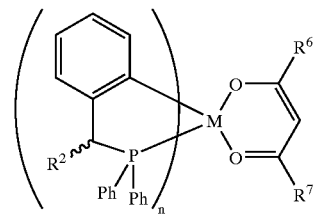

wherein:
M is selected from Ir and Pt;
Ph is a phenyl group;
$R^2$ is selected from methyl and hydrogen;
$R^6$ is an alkyl;
$R^7$ is an alkyl; and
n is 1 when M is Pt, and n is 2 when M is Ir.

17. The compound of claim 16, wherein each of $R^6$ and $R^7$ are selected from methyl and t-butyl.

18. An electronic device comprising an active layer comprising the compound of claim 16.

19. The electronic device of claim 18, wherein:
the electronic device comprises a display; and
the compound is capable of having an emission maximum in a range of approximately 420–480 nm.

20. The electronic device of claim 19, wherein the compound comprises at least approximately 20 weight percent of the active layer.

21. A compound having Formula 1:

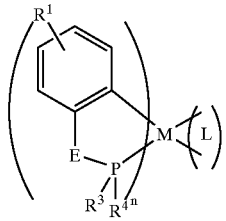

wherein:

M is selected from Ir, and Pt;

E is selected from $C(R^2)_2$, O, and $NR^2$;

L is selected from β-enolates, aminocarboxylates, iminocarboxylates, salicylates, hydroxyquinolinates and diarylphosphinoalkoxides;

$R^1$, if present, is selected from hydrogen, deuterium, halogen, alkyl, heteroalkyl, alkoxy, aryl, heteroaryl, and aryloxy;

$R^2$ is selected from alkyl, heteroalkyl, aryl, heteroaryl, and hydrogen;

$R^3$ is selected from aryl, heteroaryl, alkyl, heteroalkyl, alkoxy, and aryloxy;

$R^2$ and $R^3$ together may form a 5- or 6-membered ring;

$R^4$ is selected from aryl, heteroaryl, alkyl, heteroalkyl, alkoxy, and aryloxy; and n is selected from 1 and 2.

22. A compound having Formula 2:

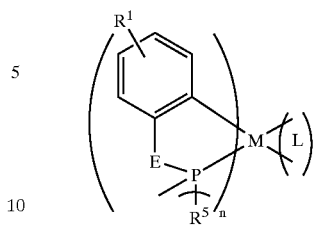

wherein:

M is selected from Os, Ru, Rh, Pd, Ir, and Pt;

E is selected from $C(R^2)_2$, O, and $NR^2$;

L comprises a monoanionic bidentate ligand;

$R^1$, if present, is selected from hydrogen, deuterium, halogen, alkyl, heteroalkyl, alkoxy, aryl, heteroaryl, and aryloxy;

$R^2$ is selected from alkyl, heteroalkyl, aryl, heteroaryl, and hydrogen;

$R^5$ is selected from alkyleneoxy, aryleneoxy, biarylene, bialkyl, bialkyloxy, and biaryloxy; and n is selected from 1 and 2.

23. The compound of claim 22, wherein L is selected form β-enolates, aminocarboxylates, iminocarboxylates, salicylates, hydroxyquinolinates and diarylphosphinoalkoxides.

24. The compound of claim 23, wherein:

E is a carbon atom; and

L comprises a β-enolate ligand selected from:
2,4-pentanedionate;
1,3-diphenyl-1,3-propanedionate;
2,2,6,6-tetramethyl-3,5-heptanedionate;
4,4,4-trifluoro-1-(2-thienyl)-1,3-butanedionate;
7,7-dimethyl-1,1,1,2,2,3,3-heptafluoro-4,6-octanedionate;
1,1,1,3,5,5,5-heptafluoro-2,4-pentanedionate;
1,1,1,5,5,5-hexaflouro-2,4-pentanedionate; and
1-phenyl-3-methyl-4-i-butyryl-pyrazolinonate.

* * * * *